United States Patent
Moreira et al.

(10) Patent No.: US 9,517,281 B2
(45) Date of Patent: Dec. 13, 2016

(54) PROCESS AND RADIATOR DEVICE FOR WORT STERILIZATION BY RADIATION FOR ETHANOL PRODUCTION

(71) Applicants: Marcelo Gianatto Moreira, Sao Paulo (BR); Airton Deppman, San Paulo (BR); Pedro Carlos Russo Rossi, Sao Paulo (BR)

(72) Inventors: Marcelo Gianatto Moreira, Sao Paulo (BR); Airton Deppman, San Paulo (BR); Pedro Carlos Russo Rossi, Sao Paulo (BR)

(*) Notice: Subject to any disclaimer, the term of this patent is extended or adjusted under 35 U.S.C. 154(b) by 0 days.

(21) Appl. No.: 14/633,043

(22) Filed: Feb. 26, 2015

(65) Prior Publication Data

US 2015/0306262 A1    Oct. 29, 2015

Related U.S. Application Data

(63) Continuation-in-part of application No. 14/462,456, filed on Aug. 18, 2014, now abandoned, which is a continuation of application No. 14/171,650, filed on Feb. 3, 2014, now Pat. No. 8,809,817, which is a continuation of application No. 13/938,219, filed on Jul. 9, 2013, now abandoned.

(30) Foreign Application Priority Data

Oct. 23, 2012    (BR) .......................... 1020120271680

(51) Int. Cl.
A61L 2/08    (2006.01)
A61L 2/10    (2006.01)

(52) U.S. Cl.
CPC . *A61L 2/10* (2013.01); *A61L 2/087* (2013.01)

(58) Field of Classification Search
USPC ...... 250/453.11, 454.11, 455.11; 422/20, 21, 422/22, 23, 24
See application file for complete search history.

(56) References Cited

U.S. PATENT DOCUMENTS

| 2004/0082899 | A1* | 4/2004 | Mathias | A61M 1/0236 604/6.16 |
| 2010/0150793 | A1* | 6/2010 | Chan | A61L 2/10 422/186.3 |
| 2011/0100885 | A1* | 5/2011 | Lee et al. | 210/85 |
| 2011/0114546 | A1* | 5/2011 | Barsky et al. | 210/143 |

* cited by examiner

*Primary Examiner* — Nicole Ippolito
(74) *Attorney, Agent, or Firm* — Galvin Patent Law LLC; Brian R. Galvin

(57) ABSTRACT

A method and irradiator apparatus used for wort sterilization by radiation for production of ethanol from sugar cane, comprising a trough-like fluid duct and a radiation source for directing radiation over the flow of a fluid conducted through the duct, and application of radiation to a fluid within an apparatus for sterilization of such fluid.

2 Claims, 4 Drawing Sheets

PROCESS AND RADIATOR DEVICE FOR WORT STERILIZATION BY RADIATION FOR ETHANOL PRODUCTION

CROSS-REFERENCE TO RELATED APPLICATIONS

This application is a continuation-in-part of U.S. patent application Ser. No. 14/462,456, entitled "PROCESS AND RADIATOR DEVICE FOR WORT STERILIZATION BY RADIATION FOR ETHANOL PRODUCTION", filed on Aug. 18, 2014, which is a continuation of U.S. patent application Ser. No. 14/171,650, entitled PROCESS AND RADIATOR DEVICE FOR WORT STERILIZATION BY RADIATION FOR ETHANOL PRODUCTION, filed on Feb. 3, 2014, now issued as U.S. Pat. No. 8,809,817 on Aug. 19, 2014, which is a continuation of U.S. patent application Ser. No. 13/938,219, entitled "PROCESS AND RADIATOR DEVICE FOR WORT STERILIZATION BY RADIATION FOR ETHANOL PRODUCTION", filed on Jul. 9, 2013, which is the national stage entry of Brazilian patent application serial number 1020120271680, filed on Oct. 23, 2012 and titled, "PROCESSO E DISPOSITIVO IRRADIADOR PARA ESTERILIZAçÃO DE MOSTO POR RADIAçÃO PARA A FABRICAçÃO DE ETANOL", the entire specifications of each of which are incorporated herein by reference in their entireties. A certified translation of the Brazilian patent application was filed with application Ser. No. 14/171,650.

BACKGROUND OF THE INVENTION

1. Field of the Invention

The invention relates to the field of ethanol production from plant-based fluids, and more particularly to application of radiation to such fluid.

2. Discussion of the State of the Art

Ethanol is an organic substance obtained from the fermentation of sugars, hydration of ethylene, or acetaldehyde reduction widely used as a process for production of fuel for engine combustion.

The "wort" is the juice of any fruit or vegetable that contains sugar, upon fermentation, and before completely purified by it. It is an intermediate product common to several processes, such as in the production of ethanol from sugar cane, sugar beets, and other vegetables. The result of fermentation of the wort is called wine. The wort is an organic fluid naturally contaminated by a range of microorganisms that will compete with the yeast incorporated into the mixture (for fermentation) in the production of ethanol. This problem is common to these techniques, and the existence of a wide range of bacteria in these plants that contaminate the wort is well known in the art. This combination is responsible for reducing bacterial productivity of these processes.

Microorganisms contaminate the process of production of alcohol, represented by bacteria and yeast that settle in the process. These contaminants are causing problems such as the consumption of sugar that would otherwise be converted into ethanol, decreased viability of yeast cells because of toxins excreted in the fluid by the microorganisms, flocculation of yeast that causes loss of yeast cells by the fund in the dressage or spin, and consequent fall in the industrial output. Furthermore, the formation of gum increases viscosity of the broth, causing operational problems in the production facility.

The juice of sugar cane contains varying amounts of organic and inorganic nutrients, high water activity, favorable pH and temperature conditions, and therefore provides for great growth of microbial flora. The very conditions of each stage of the production of alcohol select for microorganisms and the whole process is subject to contamination from the sugar cane field until the fermentation of its broth.

Yeasts and bacteria contaminants can produce lactic acid and other organic acids that, in quantities exceeding the normal, may be responsible for a decrease in the yield of fermentation. When this bacterial contamination reaches levels above $10^7$ cells/ml, a significant drop in the yield of the alcohol may occur, and out-of-control bacterial contamination may indirectly cause a reduction in yield of fermentation because of the increased viscosity of the broth causing a greater loss of yeast broth centrifuged and higher consumption of sugar, diverting this from the production of sugar and alcohol.

The form currently used to overcome this problem in the art is the addition to the wort of various antibiotics, thereby reducing bacterial contamination. However, this process entails some new drawbacks among which are:
   High cost of antibiotics
   Need for periodic study of the range of bacterial contamination
   Effects of bacterial action on yeast reduce productivity
   Continued use of antibiotics can lead to biological and environmental problems by being re-released into the environment such as with, for example, the creation of resistant bacterial species What is needed is a sterilization procedure that avoids the use of antibiotics.

SUMMARY OF THE INVENTION

Accordingly, the inventor has conceived and reduced to practice, in a preferred embodiment of the invention, a method and apparatus for wort sterilization by radiation for production of ethanol from sugar cane, comprising an autonomous principle that replaces the use of antibiotics, thereby eliminating this step in the process of production of ethanol from plant fluids. According to studies, irradiation reduces the dramatic contamination caused by bacteria and alterations of wort are also lower after irradiation contributing to a marginal increase in productivity. Among the main benefits of irradiation of wort are:
   Elimination of the need to use antibiotics
   Elimination of environmental risks generated by the combings of antibiotics in the environment
   Reduction of production costs such as total elimination of costs associated with antibiotics
   Increased productivity by eliminating the effects of bacterial action in the wort The absorption of ionizing radiation causes chemical alterations in the cellular components of microorganisms, which may have consequences for the activity of the cells. Of all the mechanisms that are involved in radiation action on cells, the alteration in a cell's DNA is considered the most important and, as a consequence of such alterations induced by radiation, cell death may be caused. Yeasts and molds have increased sensitivity to radiation compared to some non-spore-forming bacteria.

Numerous studies have also demonstrated that the combination of coolant with the irradiation causes an inhibitory effect on the multiplication of spoilage microorganisms, reducing the radiation dose required to control the proliferation of these microorganisms. A radiation dose required may also vary according to the product being to be produced, for example the dose applied to apple or grape wine may be different from that applied to sugar cane, which in turn may differ from that to be applied to orange wine.

Care should be taken with regard to wort irradiation external dose (i.e., surrounding region), internal dose (such as of the wort itself), and environmental contamination.

With respect to an external dose, caution should be taken regarding the shielding of equipment, with monitoring the level of radiation in surrounding areas; proper protective equipment is necessary particularly when personnel access is needed.

With respect to an internal dose, some care should be taken to ensure uniformity of the applied dose of the mash and the minimum dose necessary for an appropriate level of sterilization to be reached, and with respect to the environment necessary care should be taken to reduce the possibility of radioactive leakage.

Radiation sterilization is an efficient method already proven in numerous applications from irradiation of food products to irradiation of medical supplies. The use of gamma radiation, as previously mentioned, is often indicated by its greater ability to penetrate the material to be sterilized with respect to other types of radiation, such as ultraviolet (UV), or electron, proton, or neutron-based radiation types.

Irradiation with $Co^{60}$ gamma radiation from decay has proven to be effective in the sterilization of sugar cane pumice wort and a dose of about 10 kGy was possible to reduce to 10% the initial contamination of some bacteria. For comparison, radiation used in sterilization of medical equipment often utilizes a dosage of around 50 kGy. Thus, it can be appreciated that the optimal dose for sterilization of wort should fall between these two values, as an overdose of the wort could cause undesirable chemical changes. However, studies have shown that modification of the medium are smaller than those produced after the addition of antibiotics.

According to a preferred embodiment of the invention, a process of wort sterilization comprises sterilization in fluid from a radioactive source, where the fluid may be irradiated in ducts. Accordingly, the radiation can be performed in a continuous manner also incorporating fluid movement within a duct-based irradiation apparatus, as described below.

This process of irradiation need not be only restricted to the wort and can even replace other methods in various fields, such as the pasteurization of liquid foods or sterilization of contaminated gasses against pathogenic microorganisms. Radiation doses applied are different and may vary according to a particular purpose or application, and may feature two distinct forms, namely scaling of a source (i.e., the actual dose) and a fluid flow regulation in a duct apparatus, i.e. length of exposure to radiation. In general, any source or radiation may be utilized, however the as envisioned by the inventor $Co^{60}$ is utilized due to its high natural abundance.

According to another preferred embodiment of the invention, a wort irradiator apparatus is disclosed, comprising a radiation source in a container with dimensions suitable for use in a production facility, which may be installed alongside a pipeline in such a production facility. This device may function such as to eliminate microorganisms that may contaminate a wort through irradiation appropriately sized or dosed for the application and a device may be built in a modular way such as to facilitate ease of replacement or repair in the event of damaged or faulty components or device failure.

According to the embodiment, the device may comprise three distinct modules: a drum for a sealed radiation source, a container that may be used for housing a fluid, and an outer shield that may be used to cover the entire container such as to prevent external radiation leakage. The apparatus may further comprise two connections, an input and an output. An input connection may be located at the bottom of the apparatus and an output near the top. In this manner, the apparatus of the invention may be readily adapted to any existing production facility through the use these input and output connections.

According to another preferred embodiment of the invention, an apparatus for irradiation of a fluid, comprising a plurality of fluid ducts and a plurality of radiation sources, wherein the radiation sources direct radiation over at least a portion of at least some of the plurality of fluid ducts and wherein at least some of the fluid ducts direct the flow of a fluid through the path of radiation, is disclosed.

BRIEF DESCRIPTION OF THE DRAWING FIGURES

The accompanying drawings illustrate several embodiments of the invention and, together with the description, serve to explain the principles of the invention according to the embodiments. One skilled in the art will recognize that the particular embodiments illustrated in the drawings are merely exemplary, and are not intended to limit the scope of the present invention.

DETAILED DESCRIPTION

The inventor has conceived, and reduced to practice, in a preferred embodiment of the invention, a method and apparatus for wort sterilization by radiation for production of ethanol from sugar cane, comprising an autonomous principle that replaces the use of antibiotics, thereby eliminating this step in the process of production of ethanol from plant fluids.

Detailed Description of Exemplary Embodiments

Figure 1:
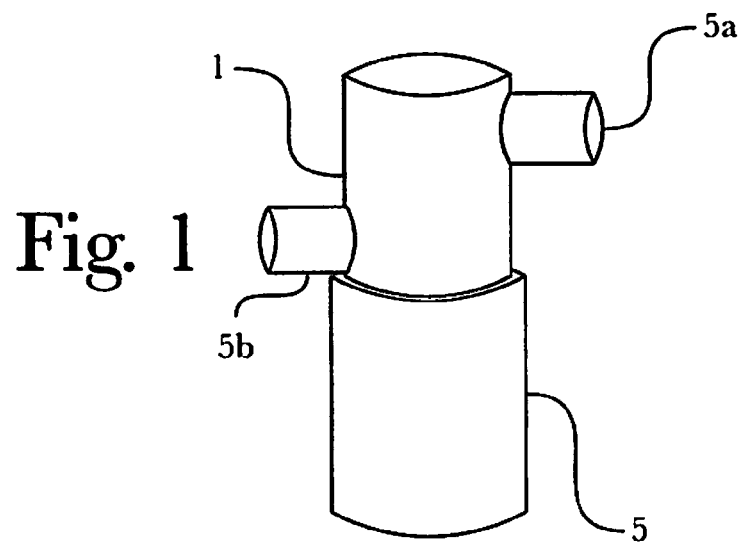
FIG. 1 is an illustration of a wort irradiator device, according to a preferred embodiment of the invention.

FIG. 1 is an illustration of a wort irradiator device, according to a preferred embodiment of the invention. As illustrated, an irradiation container 1 may be installed in a drum on top of a fluid source 5 for connection via two ducts, one inlet 5a where a wort may enter such as to undergo a sterilization process and one outlet 5b such as for exiting of a wort after sterilization.

According to the embodiments (and as illustrated in the following figures, below), a wort irradiator according to the invention may comprise a container 1, round rods 2 a radiation source 3, driving rod 4, a drum source 5, and a mixer 6, an arrangement of a source 7, spacer 8, and the entire apparatus protected by a shield casing 9.

Figure 2:
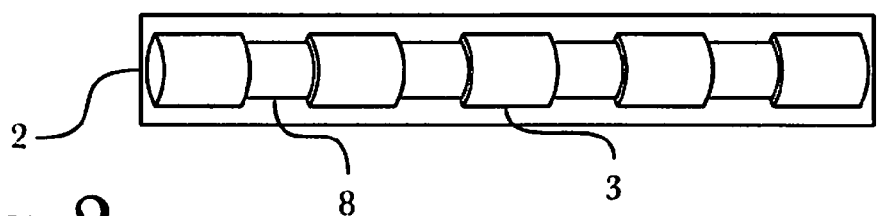
FIG. 2 is an illustration of a radiating rod containing pellets and spacers.

Referring now to FIG. 2, round rods 2 may further comprise a plurality of radiation sources 3 that may be arranged with mechanical spacers 8, such as to prevent radiation sources from coming into physical contact and to regulate a radiation dosage. Exemplary radiation sources may include (but are not limited to) Cesium-137, Iodine-131, Lanthanum-140, or any of a variety of suitable gamma radiation emission sources, as are commonly known in the art. Spacers 8 may serve to regulate total dosage of radiation, and homogeneity of irradiation applied to a wort.

Figure 3:
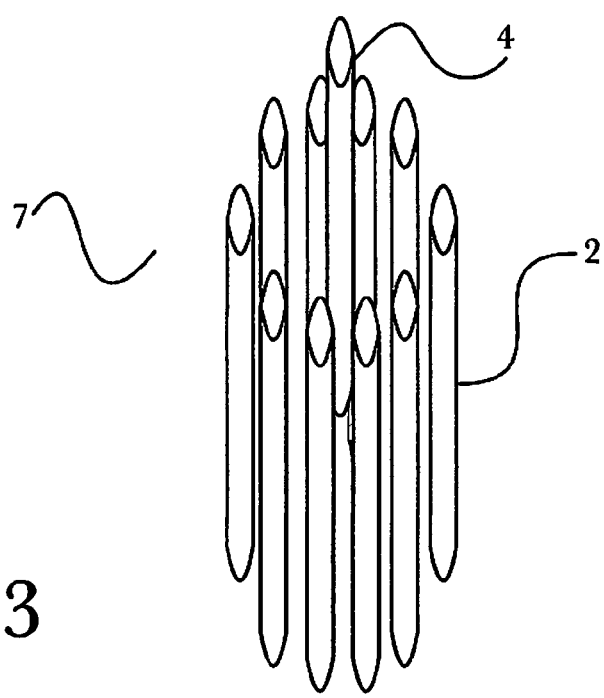
FIG. 3 is an illustration of a complete arrangement of a radioactive source containing rods.

Referring now to FIG. 3, inside a radiation container 1 may be installed an arrangement of a source 7. Such an arrangement may be formed by irradiation of cylindrical rods 2 and a driving rod 4 that may be interconnected. A number of irradiation rods 2 arranged in an array as illustrated may vary according to the invention (for example, rearranging to include more or fewer rods, or to vary the spacing or relative position of individual rods). Various vertical ducts may be fixed in an irradiation container 1 such as for separating a fluid source within the container. In this manner, it can be appreciated that a fluid may never come into direct physical contact with a radiation source and that a central duct may be reserved for movement of a driving rod 7. Cylindrical rods 2 may be connected in parallel to the bottom of a driving rod 4. This arrangement of irradiation rods 2 and driving rod 4 forms an arrangement of the source inside which radioactive sources 3 and spacers 8 may be placed.

During a sterilization process a wort may be continuously flowing inside an irradiation container 1 without the need to interrupt a grinding process. This may make a production facility's output slightly higher than that allowable by antibiotic sterilization.

Figure 4:
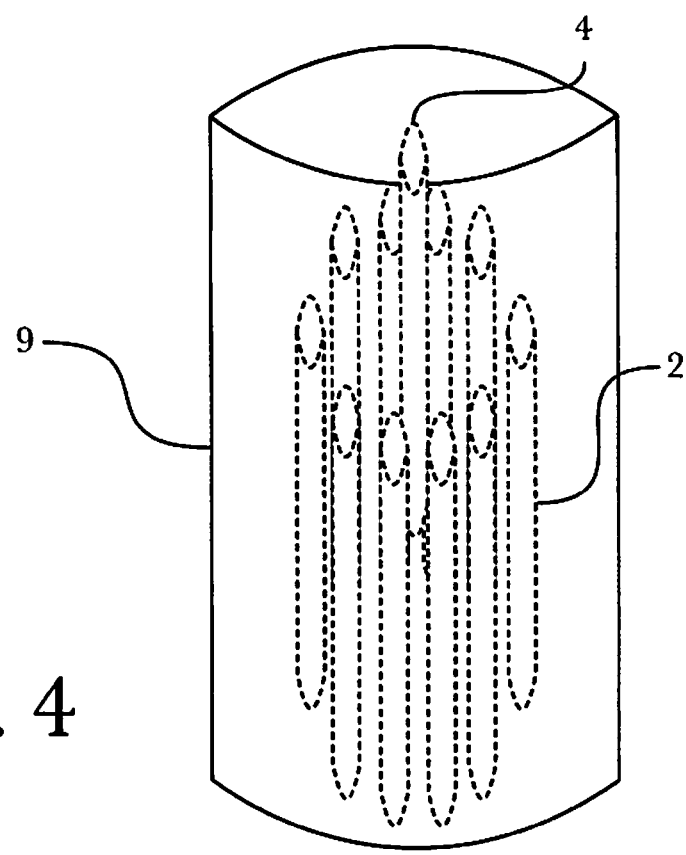
FIG. 4 is an illustration of a radioactive source drum.
Figure 5:
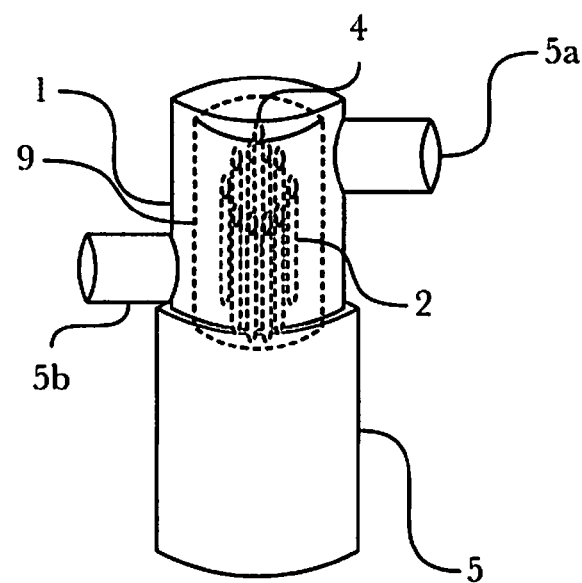
FIG. 5 is an illustration of an outer shield casing.
Figure 6:
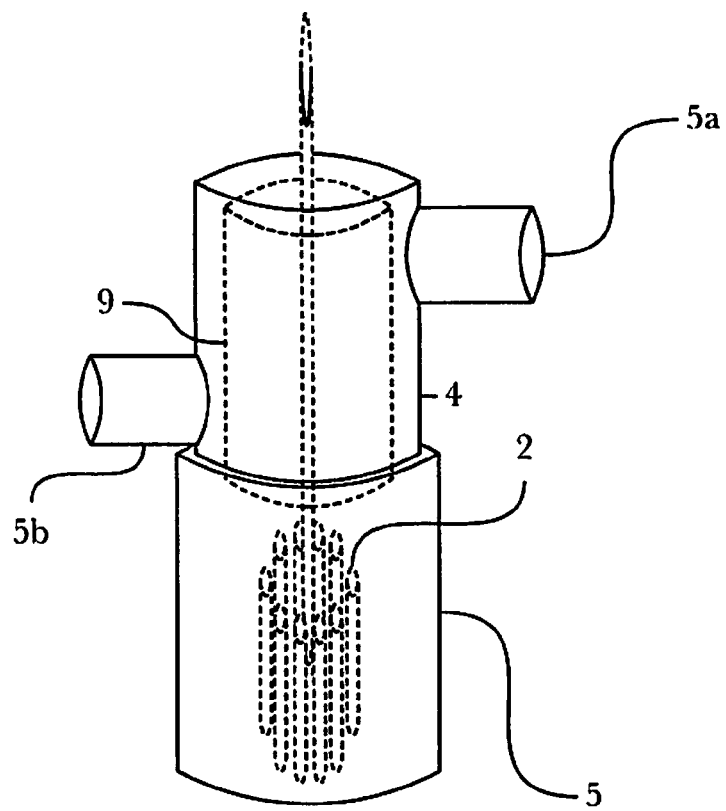
FIG. 6 is an illustration of a device mounted in the off state.
Figure 7:
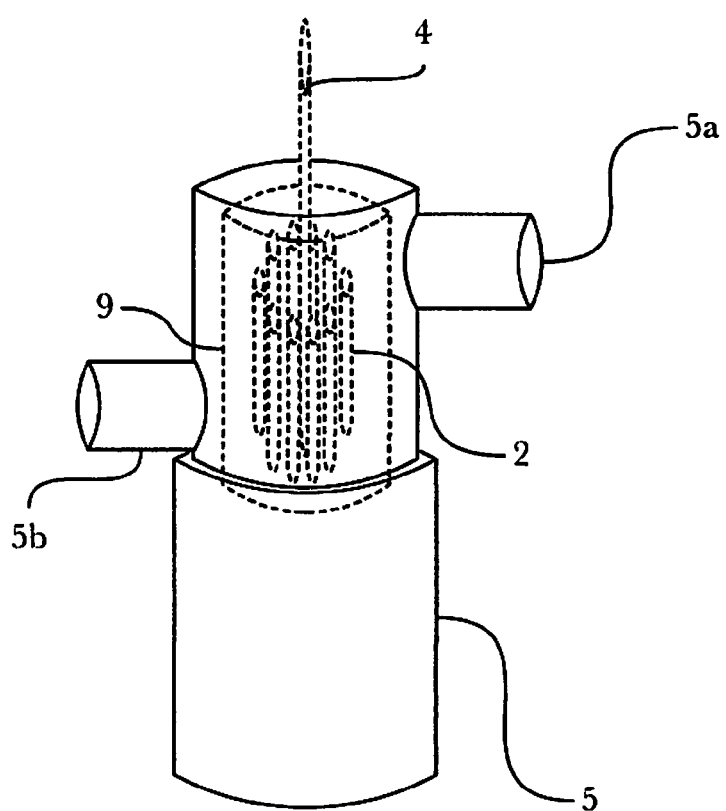
FIG. 7 is an illustration of a device in the bound state.

Referring now to FIGS. 4 and 5, an exemplary wort irradiator drum and apparatus constructed according to an embodiment of the invention are shown. In an "off" state (as illustrated in FIG. 6), an arrangement of a source 7 positioned within a drum 5 and thus radiation may be limited within its interior, that is, an input fluid (i.e., a wort) may not be irradiated. Consequently, when an apparatus is in an "on" state (as illustrated in FIG. 7), the arrangement of a source 7 may be raised by a movement rod 4 into vertical ducts set in an irradiation container 1 and therefore radiation may be applied to an internal volume of the container 1 and maintained within the inner boundaries of a shielding enclosure 9. Thus, if a fluid is input as described above, it may be irradiated within an irradiation container 1 and exit an apparatus completely sterilized.

Taking into account that safety is a factor of extreme importance, an irradiation container 1 may be designed to be affixed into the ground (such as within concrete), thus preventing the surrounding region to be affected by an elevated dose of radiation above that which is natural. It may also be designed with a mechanism such as to allow easy installation or uninstallation of equipment without risk to workers. Such a mechanism may comprise a supply drum 4, which may be isolated underneath a radiation container 1. When installing or removing an arrangement 2, it may be lowered until it is installed completely within a source drum 4. Drum 4 may then be sealed, preventing radiation leakage, and may then be safely removed from a production facility.

Figure 8:
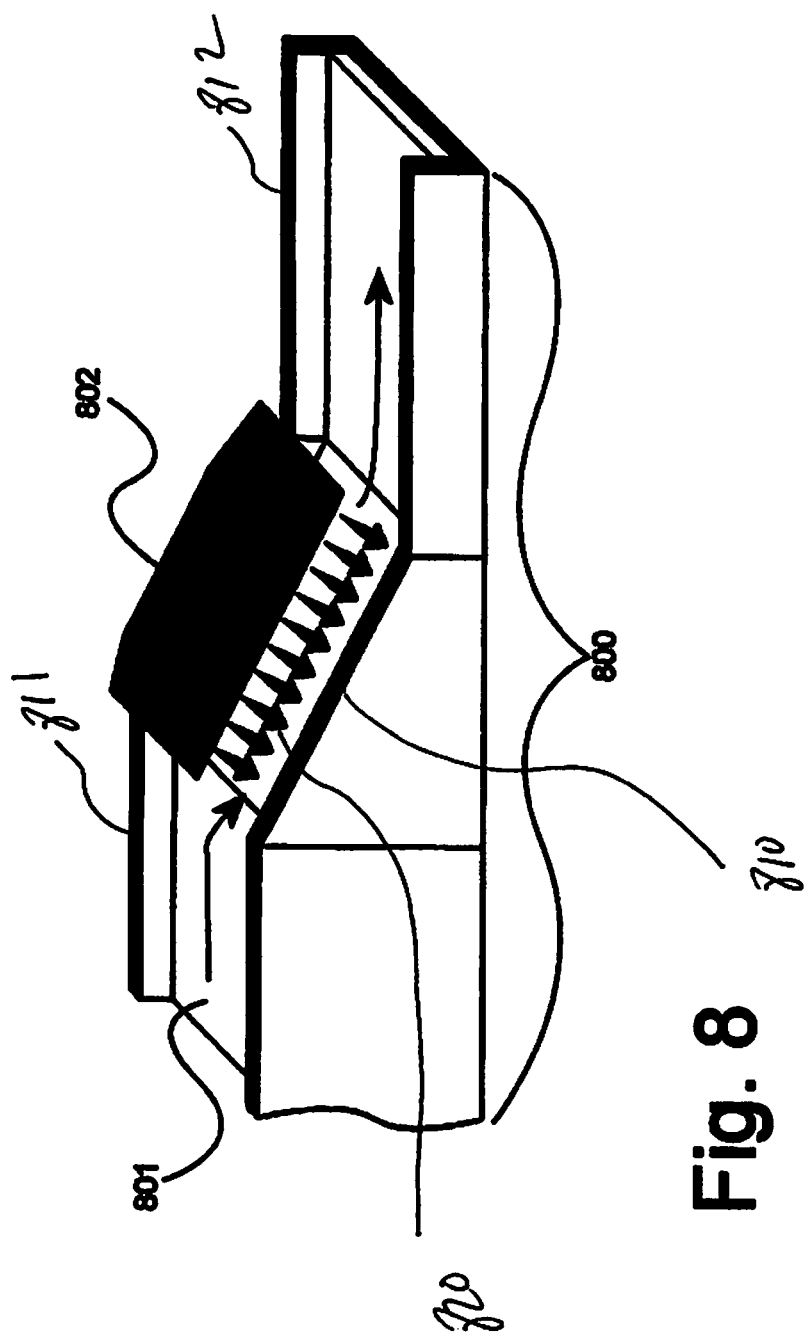
FIG. 8 is an illustration of a trough-style arrangement of a wort irradiator apparatus, according to a preferred embodiment of the invention.

FIG. 8 is an illustration of a trough-style arrangement of a wort irradiator apparatus 800, according to a preferred embodiment of the invention. According to the embodiment, a wort or other fluid may be directed to flow into a generally trough-shaped or similarly concave fluid duct 801, such that a directional flow is maintained. A radiation source 802 may be positioned above duct 801 or may be removably or integrally fixed to duct 801, ideally arranged such that the flow path of a fluid in duct 801 is directed through a path of radiation 820, and ideally such that the fluid is fully irradiated; that is, the flow path is exposed to a level of radiation for a duration so that enough radiation in aggregate is passed through the fluid transiting through duct 801 to fully sterilize the fluid as it passes beneath or through the path of radiation from radiation source 802, according to the particular arrangement and intended purpose of the embodiment (for example, for sterilization of a plant wort in the industrial scale production of ethanol). According to the embodiment, a sloped portion 810 of a duct 801 may be utilized to direct fluid from an inlet portion 811 to an outlet portion 812 to cause the fluid to flow beneath radiation source 802 and to accelerate the flow of a fluid through a corresponding radiation path (as illustrated), ensuring thorough irradiation of the fluid while maintaining a desirable rate and direction of flow for the purposes of the arrangement. Additionally, in some arrangements a radiation converter may be affixed to or may be an integral component of radiation source 802; for example a radiation source 802 may be a tantalum plate adapted to convert a gamma radiation source into a specific form or intensity of radiation such as an electron beam. In a preferred embodiment, radiation source 802 comprises an electron accelerator that focuses its beam directly on fluid passing through duct 801, which may be configured with or without scanner or electron dispersant to ensure even distribution of radiation across an affected region of duct 801. In some embodiments, a converted, such as a tantalum plate, may be used to convert gamma radiation (for example, from a fixed gamma radiation source) to an electron beam with controllable geometric intensity distribution.

In some embodiments, a plurality of integrally-formed or affixed devices such as rigid rods, movable wheels, or other such components may be utilized in duct 801, generally to induce eddies or otherwise to perturb the flow of a fluid through duct 801, as may be desirable to ensure thorough mixing of the fluid for even exposure to radiation source 802. In this manner a channel may be constructed and arranged in such a way as to facilitate rapid, directed flow of a fluid such as a plant wort while also sufficiently irradiating the wort through sufficient exposure to a radiation source 802, thereby sterilizing the plant wort more efficiently and thoroughly than may be possible through traditional means such as heating or through addition of chemicals such as antibiotics. It may be appreciated that by varying the type or intensity of radiation 820 or the exposure of a fluid to radiation source 802, various arrangements may be adapted for different purposes such as the sterilization of plant wort, juice, or beer, or for non-sterilization purposes such as to test a fluid or observe the effects of irradiation, or to alter a fluid by irradiation (for example, to dissociate a fluid or cause a substance to precipitate out of a fluid by the introduction of a specific form or intensity of radiation). It should be further appreciated that while a singular arrangement comprising a single fluid duct 801 and a single radiation source 802 is illustrated, various arrangement utilizing multiple ducts or radiation sources 802 and various combinations and arrangements thereof may be utilized according to the embodiment, such as having multiple radiation sources 802 to ensure complete irradiation of a fluid flowing through a duct, or utilizing multiple ducts to conduct fluid through radiation path 820, or other such arrangements.

In a particular embodiment, involving application in sugarcane processing plants, device 800 may be positioned before settling (decantation) vats in order to sterilize extracted liquid, minimizing the use of acids for pH control and avoiding the need to apply antibiotics for sterilization. The application of polymers to facilitate decantation may also be minimized and may even be eliminated if devices to cause whirling or eddies are utilized to ensure full mixing of fluid in channel 801. The need for liquid sterilization via heating process (thermal barrier) and decantation are also eliminated, freeing up surplus electrical energy.

The skilled person will be aware of a range of possible modifications of the various embodiments described above. For example, while some embodiments have been described in the context of ethanol production from sugarcane stock, other uses may include ethanol production from wood, corn, biowaste, or other suitable materials. For example, a plurality of fluid ducts or channels 801 may be used, each with or without eddy-inducing elements, and a plurality of radiation sources may be used, disposed collectively to ensure adequate irradiation of all fluid passing through the plurality of ducts. Also, in some embodiments duct 801 is actually a mat over which fluid, such as arterial runoff fluid, may be passed (and irradiated while passing over mat 801 by radiation from radiation source 802), for example as it exits one stage of an ethanol production process (for example, fermentation) and before it arrives at a subsequent stage (for example, settling or decantation, or purification); in such an embodiment, fluid is sterilized passively while passing over mat 801 thus eliminating need for a special sterilization process downstream. Accordingly, the present invention is defined by the claims and their equivalents.

What is claimed is:

1. An apparatus for sterilization of a fluid, comprising:
a fluid duct comprising a first horizontal portion through which fluid flows from a first end to a second end;
an inclined portion located downstream of the first horizontal portion and receiving fluid from the second end of the first horizontal portion, the fluid passing down the inclined portion and exiting at a distal end relative to the first horizontal portion;
a second horizontal portion downstream of the inclined portion and receiving fluid from the distal end; and
a gamma radiation source positioned above the inclined portion of the fluid duct;
wherein horizontal fluid flow through the fluid duct proceeds through the first horizontal portion, the inclined portion, and the second horizontal portion generally in a single horizontal direction defined by flow from the first end to the second end of the first horizontal portion; and
wherein the fluid duct conducts fluid from the first horizontal portion through the inclined portion wherein it may be sterilized by radiation to the second horizontal portion.

2. An apparatus for irradiation of a fluid, comprising:
a plurality of fluid ducts; and
a plurality of gamma radiation sources;
wherein the gamma radiation sources direct gamma radiation over at least a portion of at least some of the plurality of fluid ducts;
wherein horizontal fluid flow through the fluid duct proceeds through a first horizontal portion, an inclined portion, and a second horizontal portion generally in a single horizontal direction defined by flow from a first end to a second end of the first horizontal portion; and
wherein at least some of the fluid ducts direct the flow of a fluid through the path of gamma radiation.

* * * * *